(12) United States Patent
Obrea et al.

(10) Patent No.: US 8,891,812 B2
(45) Date of Patent: Nov. 18, 2014

(54) SECURE PRESCRIPTION COMPUTER FOR GENERATING PRESCRIPTIONS THAT CAN BE AUTHENTICATED AND VERIFIED

(75) Inventors: Andrei Obrea, Seymour, CT (US); Christian Crews, Fairfield, CT (US)

(73) Assignee: Pitney Bowes Inc., Stamford, CT (US)

( * ) Notice: Subject to any disclaimer, the term of this patent is extended or adjusted under 35 U.S.C. 154(b) by 1273 days.

(21) Appl. No.: 11/595,413

(22) Filed: Nov. 9, 2006

(65) Prior Publication Data
US 2008/0112615 A1 May 15, 2008

(51) Int. Cl.
*G06K 9/00* (2006.01)
*G07D 7/20* (2006.01)

(52) U.S. Cl.
CPC .......... *G07D 7/2033* (2013.01); *G06K 9/00577* (2013.01)
USPC ............ 382/100; 382/321; 382/272; 382/128

(58) Field of Classification Search
USPC .......................................... 382/321, 100, 272
See application file for complete search history.

(56) References Cited

U.S. PATENT DOCUMENTS

| | | | |
|---|---|---|---|
| 5,612,889 A | | 3/1997 | Pintsov et al. |
| 5,838,814 A * | | 11/1998 | Moore .......................... 382/115 |
| 6,785,405 B2 * | | 8/2004 | Tuttle et al. ................... 382/112 |
| 6,793,723 B2 | | 9/2004 | Auslander et al. |
| 7,016,524 B2 * | | 3/2006 | Moore .......................... 382/137 |
| 7,054,461 B2 * | | 5/2006 | Zeller et al. ................... 382/100 |
| 2005/0114667 A1 * | | 5/2005 | Haas .............................. 713/176 |
| 2005/0114668 A1 * | | 5/2005 | Haas et al. ..................... 713/176 |
| 2005/0129270 A1 * | | 6/2005 | Prakash ........................ 382/100 |
| 2005/0258246 A1 * | | 11/2005 | Wolff et al. ................... 235/454 |
| 2006/0020802 A1 * | | 1/2006 | Haas et al. .................... 713/176 |
| 2006/0109515 A1 * | | 5/2006 | Zhao et al. ................... 358/3.28 |
| 2006/0126094 A1 * | | 6/2006 | Haas et al. ................... 358/1.14 |

OTHER PUBLICATIONS

IEEE Transactions on Pattern Analysis and Machine Intelligence, vol. 27, No. 3, Mar. 2005, Enhanced Perceptual Distance Functions and Indexing for Image Replica Recognition.
MED Inform, (Month 2003) vol. 0, No. 0, 00-00 Security Issues in the Electronic Transmission of Prescriptions.
Healthcare Computing 2004, The Secure Electronic Transfer of Prescriptions.
M. Kivanc Mihcak to Ramarathnam Venkatesan "New Iterative Geometric Methods for Robust Perceptual Image Hashing", Nov. 6, 2001.

\* cited by examiner

*Primary Examiner* — Jayesh A Patel
(74) *Attorney, Agent, or Firm* — Brian A. Lemm; Charles R. Malandra, Jr.; Steven J. Shapiro

(57) ABSTRACT

A method to secure unique information about a handwritten document and to provide verification of document's authenticity, integrity and non-repudiation. The method includes the following steps: creating a document having an area of interest containing information, segmenting the area of interest on the document into a plurality of elements, obtaining the average gray scale of each element, inserting the average gray scale of each element into an identifier, and attaching the identifier to the document.

15 Claims, 15 Drawing Sheets

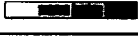
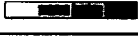
FIG. 6F
FIG. 6E

SECURE PRESCRIPTION COMPUTER FOR GENERATING PRESCRIPTIONS THAT CAN BE AUTHENTICATED AND VERIFIED

FIELD OF THE INVENTION

This invention relates generally to the field of the preparation of prescriptions and more particularly to the preparation of secure medical prescriptions.

BACKGROUND OF THE INVENTION

A prescription is a written document which contains directions for the preparation and administration of a remedy. Prescriptions originated at the beginning of history, when there were medications and a writing system to capture directions for their preparation and usage.

Modern prescriptions evolved with the separation of the role of the pharmacists, lens maker, dental technician, etc. from that of the physician, optician, or dentist. A prescription may direct a pharmacist to mix or compound medications in the pharmacy for the specific needs of the patient, or direct a lens maker to prepare optical lenses having particular characteristics. Prescriptions may also be used by dentists to direct dental technicians to prepare crowns as directed.

Pharmacists and physicians are regulated professions in most jurisdictions. A prescription as a communications mechanism between them is also regulated and is a legal document. Regulations may define what constitutes a prescription, the contents and format of the prescription. States may require that a prescription contain the following elements: the name or names and address of the patient or patients; the name and quantity of the drug or device prescribed and the directions for use; the date of issue of the prescription; the name, address, and telephone number of the prescriber, his or her license classification, and his or her federal registry number, if a controlled substance is prescribed; a legible, clear notice of the condition for which the drug is being prescribed, if requested by the patient or patients; and the signature of the prescriber issuing the order.

Currently, prescriptions are written on stationary paper pads. Thus, one of the problems of the prior art is that it is difficult for the pharmacist to authenticate the signature of the prescriber on the prescription or to identify that the same prescription was not reused.

Prescriptions are sometimes forged because someone may be a hypochondriac and a prescriber may not be willing to write a prescription for the hypochondriac. More often drug addicts, or drug pushers forge prescriptions for narcotics, because the narcotics may not be otherwise available, the narcotics are cheaper and safer as prescription drugs than as street drugs. Thus, an additional problem of the prior art is to reduce the amount of forged prescriptions.

Another problem of the prior art is that the holder of a valid prescription may change some of the information on the prescription, i.e., change the dosage of the prescribed medication from 10 mg to 100 mg, etc.

SUMMARY OF THE INVENTION

This invention overcomes the disadvantages of the prior art by enabling a pharmacist to authenticate and verify the integrity of a handwritten prescription or to prevent the use of the prescription more than once. The invention also enables the pharmacists to detect some fraudulently written prescriptions. The foregoing may be accomplished by applying a computer indicium to a prescriber's handwritten prescription. Thus, the pharmacy will have the means to verify that the indicium is valid and the indicium matches the prescriber shown on the prescription.

It would be obvious to one skilled in the art that this invention may be used for documents other than prescriptions such as birth certificates, citizenship papers, baptismal certificates, licenses, deeds, stock certificates, car titles, medical records, passports, school transcripts and admission papers, purchase receipts, military discharge papers, baptismal and death certificates, marriage licenses, divorce papers, contracts, real estate assignments and related papers, insurance policies, banking and financial records, checks, intellectual property transfer agreements and patents, personnel records, court papers, warranties, income tax returns, accounts receivable files, invoices, wills, other legal documents, etc An advantage of the invention is that the pertinent information regarding the transaction, i.e., application of the indicium may be communicated to a data center. Thus, the pharmacy may verify with the data center that the prescription is not being replayed, meaning that the prescription was not previously filled and prevent the use of copies of the prescription.

An additional advantage of this invention is the digital signature in the indicium will also prevent the prescriber's office from denying that the prescription was written by his office in cases where multiple prescriptions are written for narcotics or controlled substances.

A still further advantage of this invention is that an area of interest on the prescription may be analyzed to determine if the prescription was modified. An additional advantage of this invention is that an area of interest on the prescription may be generated by a computer.

BRIEF DESCRIPTION OF THE DRAWINGS

FIG. 6A is a drawing of a prescription containing a reference strip, used in an embodiment of this invention using gray scale profile (GSP) algorithm;

FIG. 6B is a drawing of a prescription illustrating the segmentation of area of interest into elements, used in an embodiment of this invention using gray scale profile (GSP) algorithm;

FIG. 6C is a drawing of a prescription illustrating the assignment of gray levels for each element to the closest reference gray level found on the reference strip, used in an embodiment of this invention using gray scale profile (GSP) algorithm;

FIG. 6D is a drawing of a prescription illustrating the assignment of index numbers corresponding to the closest reference gray level, used in an embodiment of this invention using gray scale profile (GSP) algorithm;

FIG. 6E is a drawing of an altered prescription, used in an embodiment of this invention using gray scale profile (GSP) algorithm;

FIG. 6F is a drawing of an altered prescription illustrating the segmentation of area of interest into elements, used in an embodiment of this invention using gray scale profile (GSP) algorithm;

FIG. 6G is a drawing of an altered prescription illustrating the assignment of gray levels for each element to the closest reference gray level found on the reference strip, used in an embodiment of this invention using gray scale profile (GSP) algorithm;

FIG. 6H is a drawing of an altered prescription illustrating the assignment of index numbers corresponding to the closest reference gray level, used in an embodiment of this invention using gray scale profile (GSP) algorithm;

DETAILED DESCRIPTION OF THE PREFERRED EMBODIMENT

Figure 1:
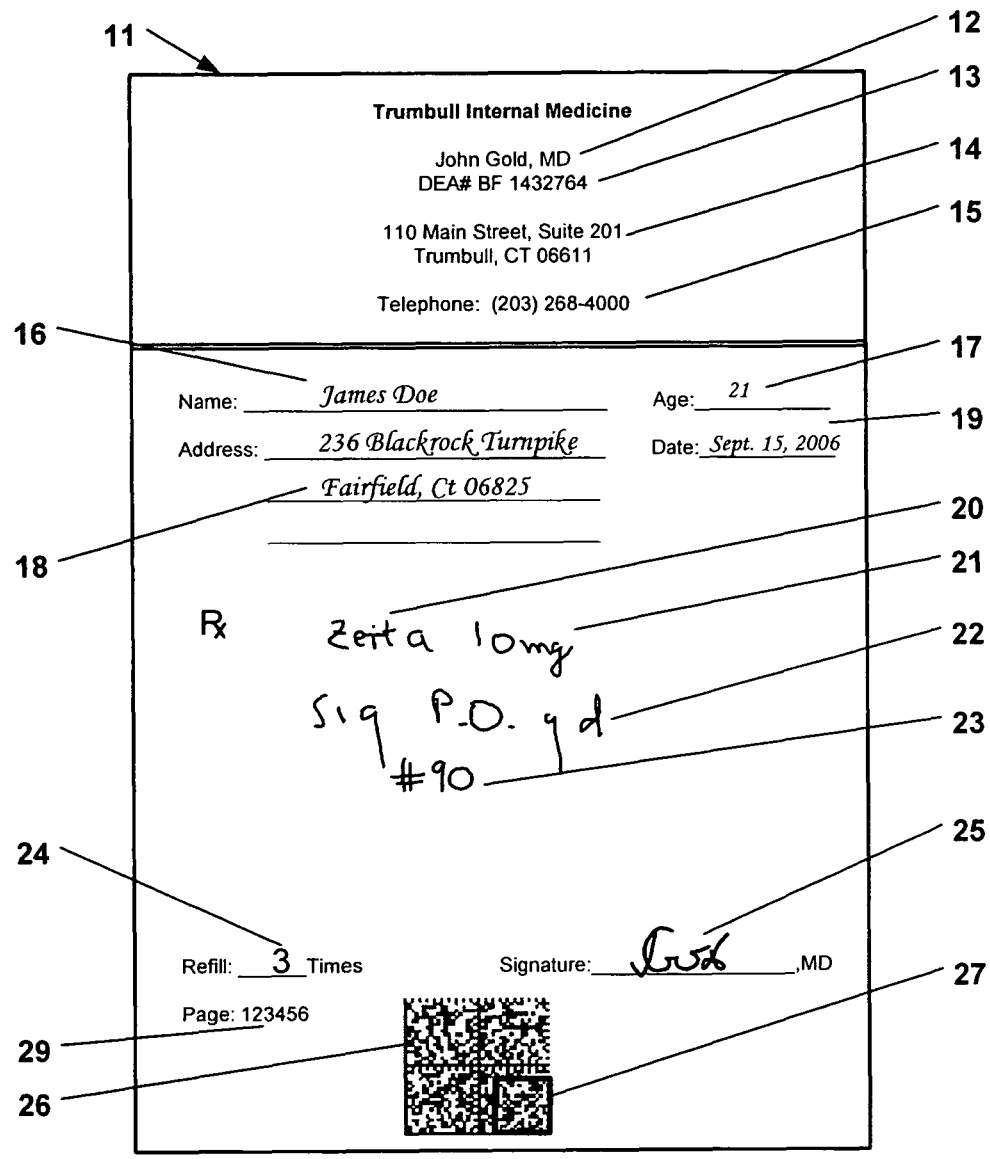
FIG. 1 is a drawing of a medical handwritten prescription.

Referring now to the drawings in detail and more particularly to FIG. 1, the reference character 11 represents a document that is a medical prescription. Prescription 11 indicates the name of the prescribing physician 12, the license classification and license number 13 of the prescribing physician, the physician's address 14 and telephone number 15. Prescription 11 also indicates the name of the patient, the patient's address 18 and the patient's age 17. The date the prescription was written is shown in space 19. The medication prescribed namely Zeita is shown at 20 and the dosage of the medication is indicated at 21. Instructions', regarding the use of the Zeta is written in an abbreviated format at 22. The abbreviated format indicates that the pharmacists should write on the label of the bottle containing Zeita (not shown), that the medication should be taken orally once a day. Space 23 indicates that 90 tablets should be supplied each time the prescription is filled and space 24 indicates that the prescription may be filed three times. The physician's signature appears in space 25 and an identification indicium or code 26 is placed on prescription 11. Identification code 26 may be represented by printed alphanumeric characters, a linear bar code, a two-dimensional bar code, glyphs, information stored in an radio frequency identification device (RFID) attached to the prescription or otherwise attached to the prescription. Code 26 may be printed on prescription 11 with a black ink, colored ink, toner, invisible ink, black fluorescent ink, etc. or affixed to a label that is attached to prescription 11. A black fluorescent ink is disclosed in the Auslander et al. U.S. Pat. No. 6,793,723 entitled "Homogeneous Photosensitive Optically Variable Ink Compositions For Ink Jet Printing" herein incorporated by reference.

Code 26 includes a digital signature 27 of specified information. The digital signature does not hide the content of the information. The digital signature verifies the content of the information by authenticating someone who is in possession of the signing key for code 26. Thus, the digital signature supports authentication and non-repudiation. Code 26 establishes that someone who signed the prescription had access to the prescription computer 9 (FIG. 2) that was assigned to the medical office that issued the prescription and indicates that the prescription came from an indefinable user of the prescription computer 9. Hence, the digital signature will also prevent the physicians' office from denying that the prescription was written by his office. Code 26 may be encrypted to hide the information and prevent unauthorized disclosure.

In one embodiment of the invention code 26 may include the serial number of the prescription computer that printed code 26, the value of a counter which the prescription computer increments after each code 26 impression and the digital signature of the above. Thus, code 26 will be a unique identifier.

In another embodiment of the invention in addition to the information contained in the aforementioned paragraph, the information covered by the digital signature for code 26 may also include the date and time when the code 26 was printed.

Each page of prescription 11 may also have a unique identifier 29 printed on it. Unique identifier 29 is unique over a defined domain which can be as narrow as the batch of printed prescriptions 11 on individual pads, or as wide as a globally unique identifier. Unique identifiers are disclosed in the Pintsov U.S. Pat. No. 5,612,889 entitled "Mail Processing System With Unique Mailpiece Authorization Assigned In Advance Of Mailpieces Entering Carrier Service Mail Processing Stream", herein incorporated by reference. Usually, to ensure uniqueness over a wider domain, the length of the identifier needs to be increased.

When this invention uses a unique identifier 29 for each individual page of prescription 11, identifier 29 is made available to computer 35 (FIG. 2) which calculates the digital signature of the information obtained by concatenating several pieces of information which together make up the payload. This is referred to in block 107 of FIG. 5A. The unique identifier 29 can be either entered manually into computer 35 (FIG. 2), or entered using a scanner 82 (FIG. 4) followed by Optical Character Recognition (OCR), calculated in sequence based on a simple protocol of incrementing the previous number or using a barcode scanner (not shown).

Figure 5A:
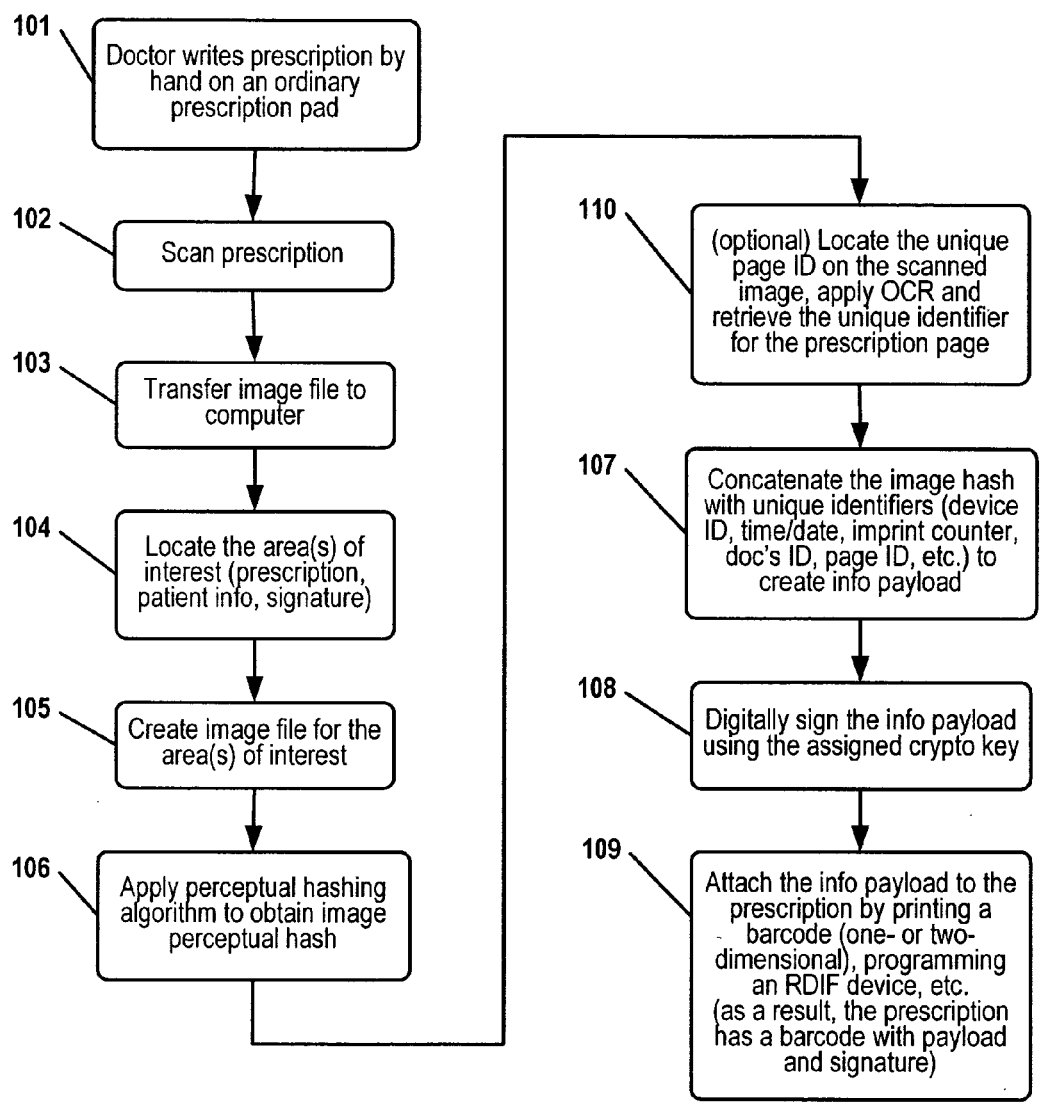
FIG. 5A is a flowchart that describes an embodiment of the invention using perceptual hashing algorithm, specifically the process to secure the handwritten prescription 11 for the purpose of authentication, integrity and to prevent replay.
Figure 5B:
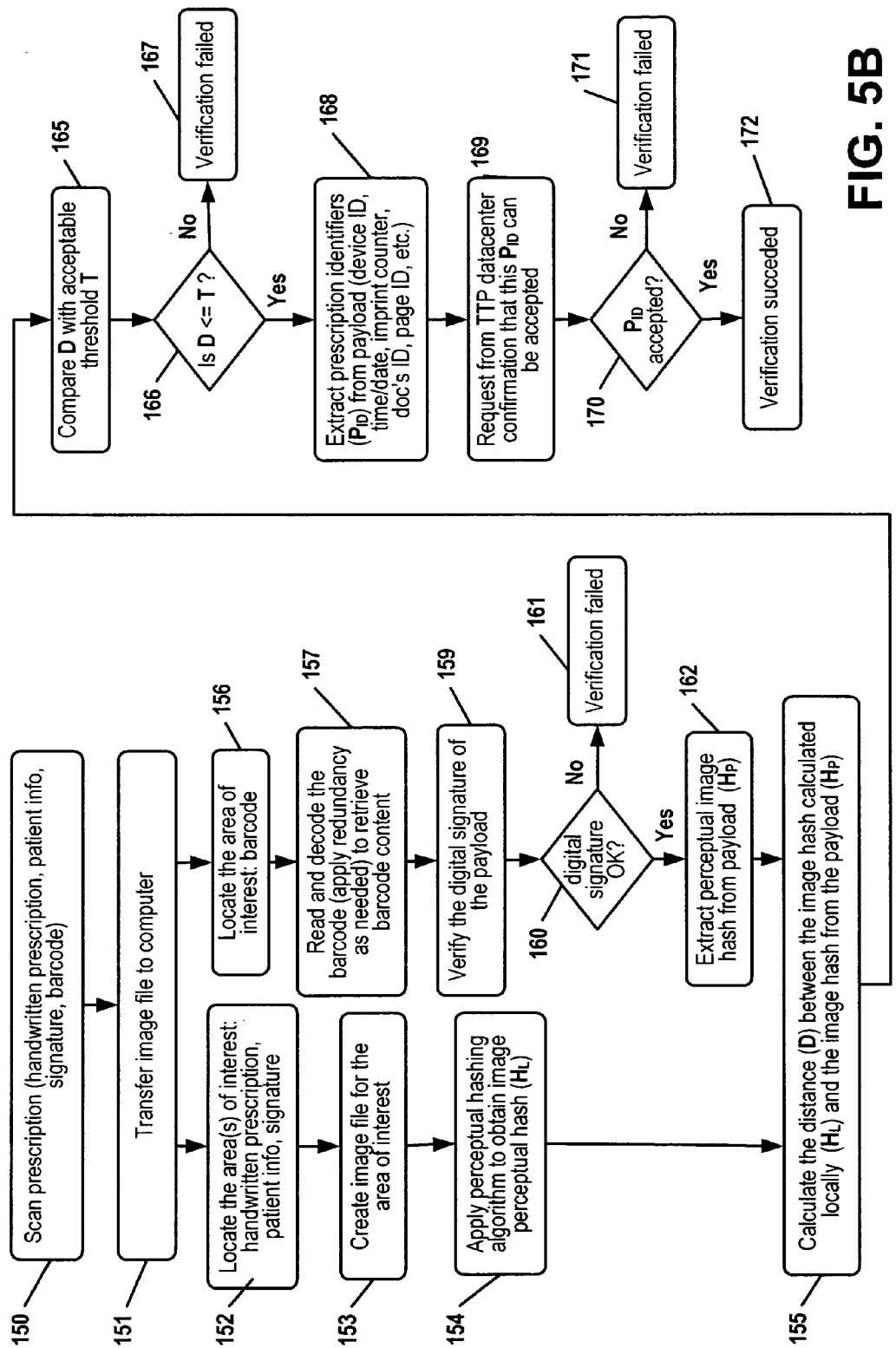
FIG. 5B is a flowchart that describes an embodiment of the invention using perceptual hashing algorithm, specifically the pharmacy's process to verify the handwritten prescription 11 authentication, integrity and to prevent replay.

The verification steps of the unique identifier 29 are shown in FIG. 5B, step 168 where the unique identifier 29 is retrieved from the payload and in step 170 it is compared with the identifier printed on the prescription 11 presented to the pharmacy. The foregoing process may also be used to verify that the code 26 matches the prescription to which it is affixed.

Figure 2:
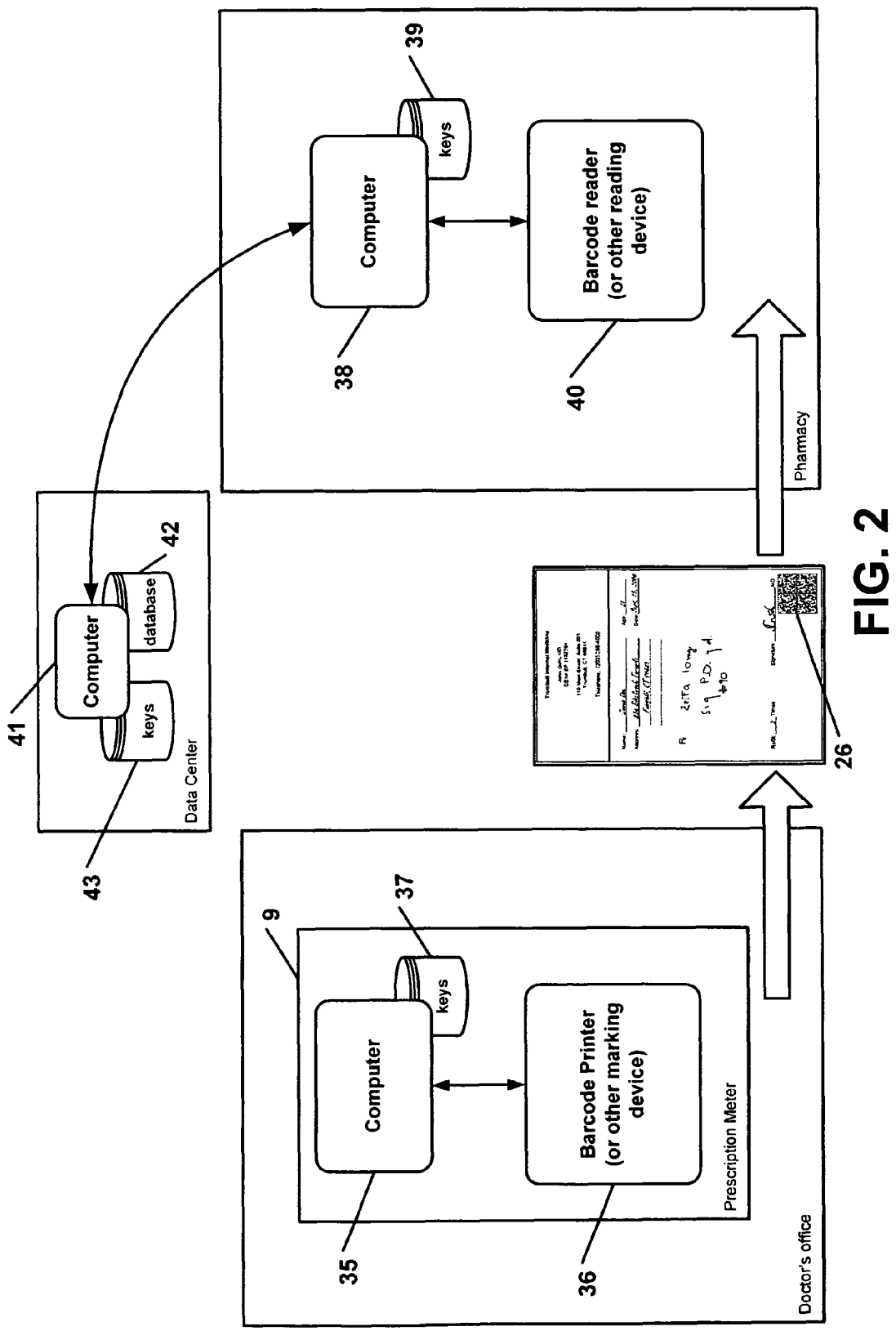
FIG. 2 is a block diagram of this invention.

FIG. 2 is a block diagram of an embodiment of this invention. This embodiment provides for the verification of the authenticity and non-repudiation of the document. Secure device 9 contains prescription computer 35, bar code printer 36 and cryptographic keys 37. Device 9 insures that printer 36 is used only under the control of computer 35 and each instance of printing code 26 contains a unique identifier and a digital signature. Prescription computer 35 may be used to generate code 26 digitally signed using keys 37, to print code 26 on prescription 11 utilizing printer 36 or any other marking device. After barcode reader 40 or other reading device scans code 26, information contained in code 26 may be sent from computer 38 to data center computer 41 and stored in data center data base 42. The information may be a unique identifier of secure device 9, for example the serial number of computer 35, the value of a counter within computer 35, which increments after each impression of code 26 and the digital signature of the above. The manner in which code 26 and the digital signature is obtained will be described in the description of FIG. 3A.

The patient for whom prescription 11 was written or their designee will take prescription 11 to a pharmacy, where bar code 26 of prescription 11 will be scanned and transmitted to pharmacy computer 38. The digital signature 27 included in code 26 may be verified by applying the appropriate cryptographic algorithms either by the pharmacy's computer 38 using keys 39 or by computer 41 using keys 43. The manner in which code 26 and the digital signature is verified will be described in the description of FIG. 3B when pharmacy computer 38 verifies the digital signature and in the description of FIG. 3C when data center computer 41 verifies the digital signature. As a result the pharmacy will be assured that the serial number of prescription computer 35 that printed code 26, and the value of a counter which prescription computer 35 increments after each code 26 impression came from a trusted source, i.e., the prescription computer 35.

The cryptographic algorithms for digital signatures used to implement this invention include, but are not limited to, public key cryptography (for example: RSA algorithms, elliptic curves algorithms), symmetric key, etc.

Computer 38 will transmit the record that indicates the prescription identified by code 26 has been used at a given pharmacy to data center computer 41. The foregoing prevents reuse of prescription 11, at a later time in the same or different pharmacy.

Figure 3A:
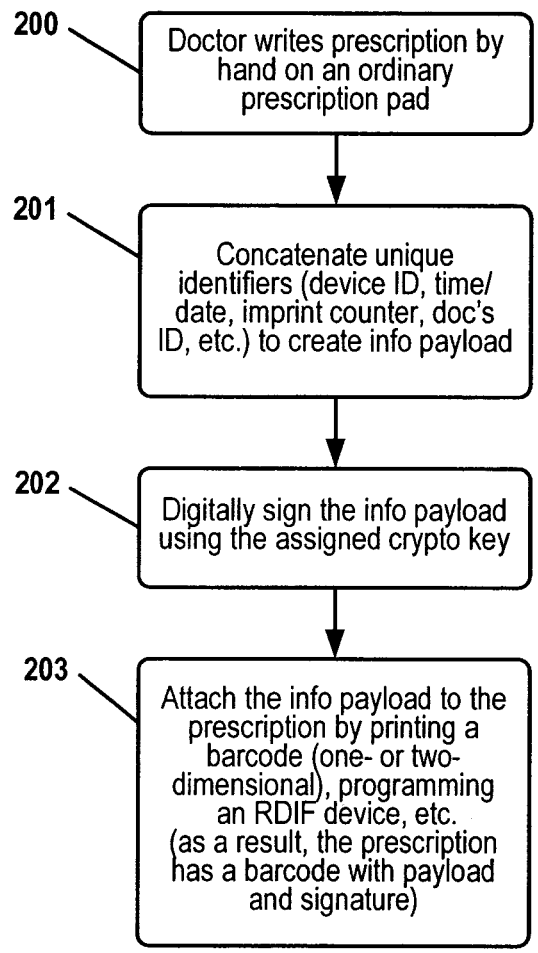
FIG. 3A is a flowchart that describes the process to secure the handwritten prescription 11 for the purpose of authentication and to prevent replay.

FIG. 3A is a flow chart that describes the process to secure the hand written prescription 11 using only authentication. The process begins at step 200, where a physician writes prescription 11 by hand on an ordinary prescription pad. Step 201 concatenates the unique identifiers of prescription computer 35, i.e., time/date, the count number of a counter in computer 35, the physician's identification etc. to create an information payload. Next in step 202 prescription computer 35 digitally signs the information payload using the assigned cryptographic key found in keys 37. Now, in step 203 the information payload is attached to the prescription 11 by printing barcode 26, which may be a one or two dimensional on prescription 11. The information payload may also be programmed into a radio frequency identification device (RFID) attached to prescription 11.

Figures 3B, 3C:
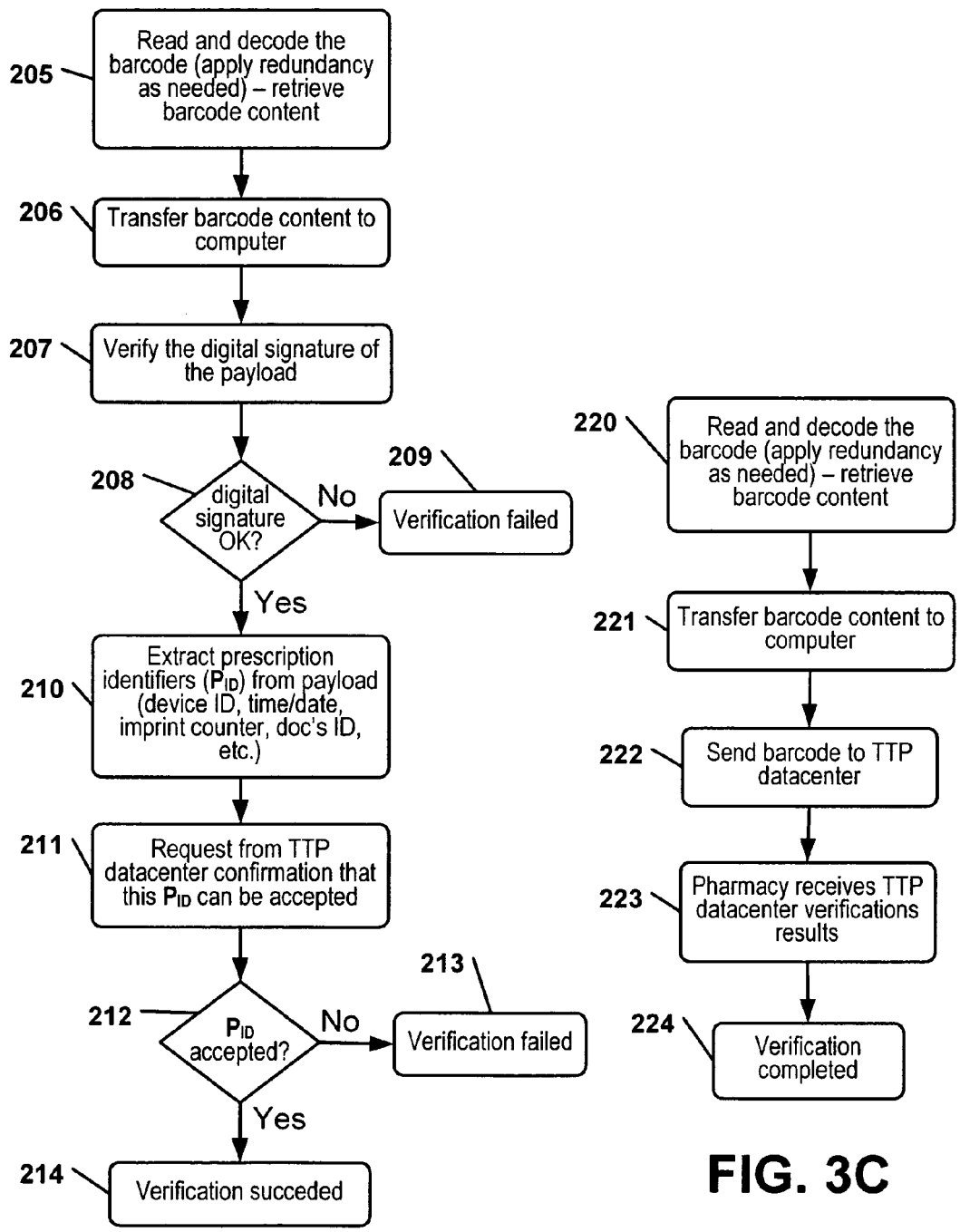
FIG. 3B is a flowchart that describes the pharmacy's process to verify the authenticity and prevent the replay of the handwritten prescription 11, when the pharmacy verifies the digital signature on the prescription.
FIG. 3C is a flowchart that describes the pharmacy's process to verify the authenticity and prevent the replay of the handwritten prescription 11, when a data center verifies the digital signature on the prescription.

FIG. 3B is a flow chart that describes the process which takes place in a pharmacy to verify the authenticity and validity of the handwritten prescription 11, when the pharmacy verifies the digital signature on the prescription and uses a trusted third party (TTP) datacenter to determine if the prescription can be accepted. The datacenter in most cases is a remote, distinct, facility, but it can be understood that in the most trivial case, the datacenter can be a computer system located in the pharmacy. The process begins in step 205, where barcode reader 40 scans barcode 26 on prescription 11 and applies any needed redundancy in order to retrieve the content of barcode 26. Next, in step 206 barcode reader 40 transfers the content of barcode 26 to computer 38. Then in step 207 the digital signature of the payload is verified by computer 38. At this point step 208 determines whether or not the digital signature is valid. If step 208 determines that the digital signature is not valid step 209 will indicate that verification has failed and there is something wrong with prescription 11. If step 208 verifies that the digital signature is fine then step 210 will extract prescription 11 identifiers ($P_{ID}$) from the payload i.e., identification of computer 35, time/date, the value of a counter in computer 35 that is contained in barcode 26, the physician's identification, etc. Next in step 211 computer 38 requests from data center computer 41 confirmation that this ($P_{ID}$) can be accepted. Step 212 determines whether or not ($P_{ID}$) can or cannot be accepted. If step 212 determines that ($P_{ID}$) can not be accepted then in that event step 213 will indicate that verification has failed and there is something wrong with prescription 11. If step 212 determines that ($P_{ID}$) may be accepted then step 214 will indicate that verification has succeeded.

FIG. 3C is a flow chart that describes the process which takes place in a pharmacy to verify the authenticity and validity of a hand written prescription 11, when a data center is used to verify both the digital signature on the prescription 11 and the fact that the prescription can be used. The process begins in step 220 where barcode reader 40 reads and decodes barcode 26 and applies any redundancy as needed in order to retrieve the content of barcode 26. Then in step 221 barcode reader 40 transfers the content of barcode 26 to computer 38. Now in step 222 computer 38 transmits the content of barcode 26 to data center computer 41. Then in step 223 pharmacy computer 38 receives the verification results of barcode 26 from data center computer 41. Then step 224 indicates that the verification results have been completed.

Figure 3D:
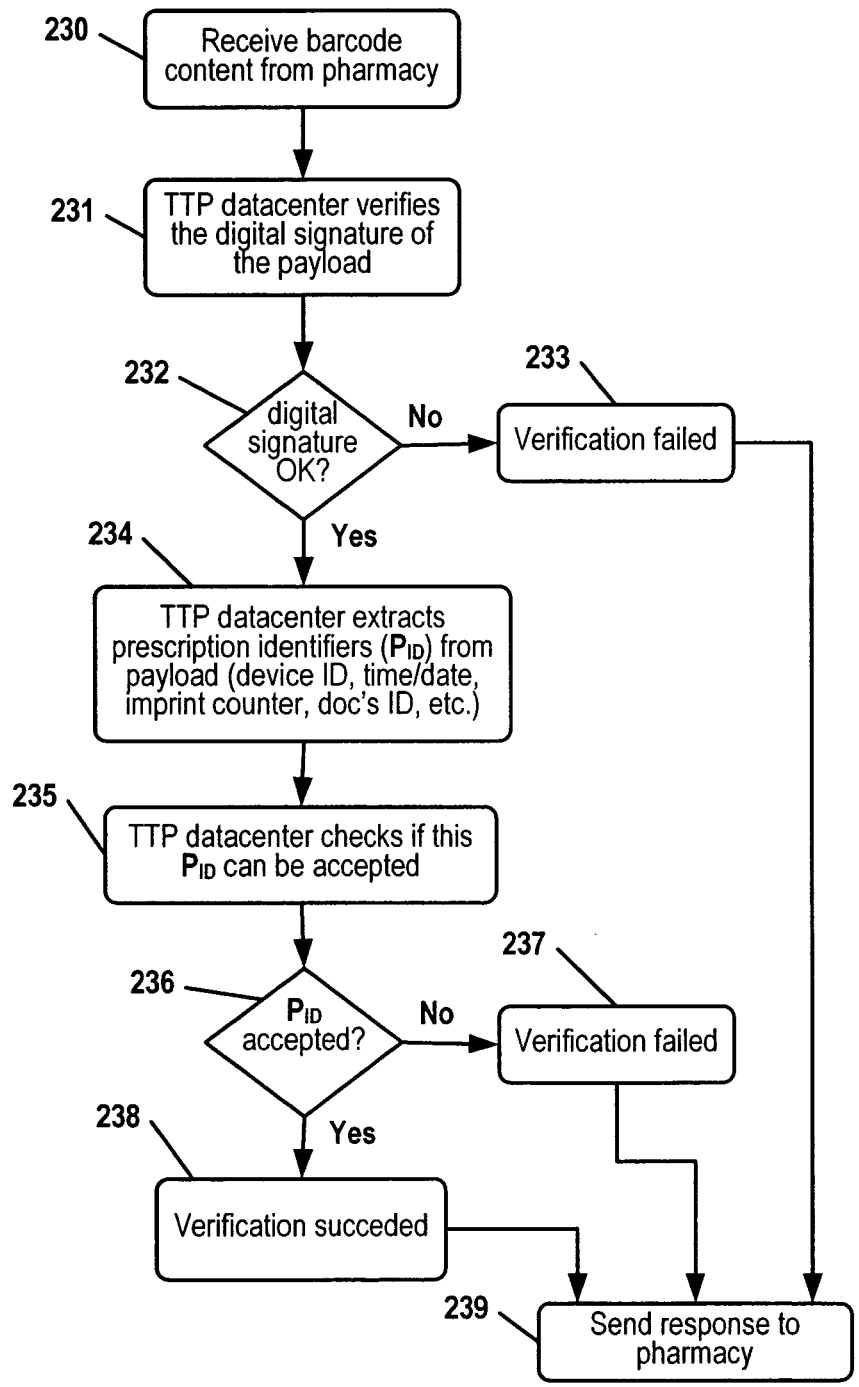
FIG. 3D is a flowchart that describes the data center's process to verify the authenticity and prevent replay of the handwritten prescription 11, when a data center verifies the digital signature.

FIG. 3D is a flow chart that describes the process which takes place in a datacenter to verify the authenticity and validity of the hand written prescription 11, when a data center verifies the digital signature and validity on the prescription. The process begins in step 230 where data center computer 41 receives the content of barcode 26 from pharmacy computer 38. Then in step 231 data center computer 41 calculates the digital signature on the payload. Next step 232 determines whether or not the digital signature is verified. If step 232 determines that the digital signature is not verified then step 233 will indicate that verification has failed. The indication that verification has failed will be sent to step 239 so that a response may be transmitted to pharmacy computer 38. If step 232 determines that the digital signature is fine then the next step will be step 234. In step 234 data center computer 41 extracts prescription identifiers ($P_{ID}$) from the payload created by computer 35 i.e., identification of computer 35, time/date, the number printed by a counter contained in prescription computer 35, the physician's identification, etc. Next, in step 235 data center computer 41 checks to see if this ($P_{ID}$) can be accepted. Then step 236 determines whether or not ($P_{ID}$) may or may not be accepted. If step 236 determines that ($P_{ID}$) cannot be accepted then step 237 will indicate that verification has failed. The criteria for accepting the payload is given by the rules of the application, for example, a prescription cannot be used beyond the number of refills allowed. It is understood that the pharmacy may transmit to the datacenter, along with the content of code 26, additional information (for example refill count as written on the prescription) to support such decisions. Step 239 will then transmit a response to pharmacy computer 38 indicating that verification has failed. If step 236 determines that ($P_{ID}$) is accepted then step 238 will indicate that verification has succeeded. Now an indication of the successful verification will be sent in step 239 to pharmacy computer 38.

Figure 4:
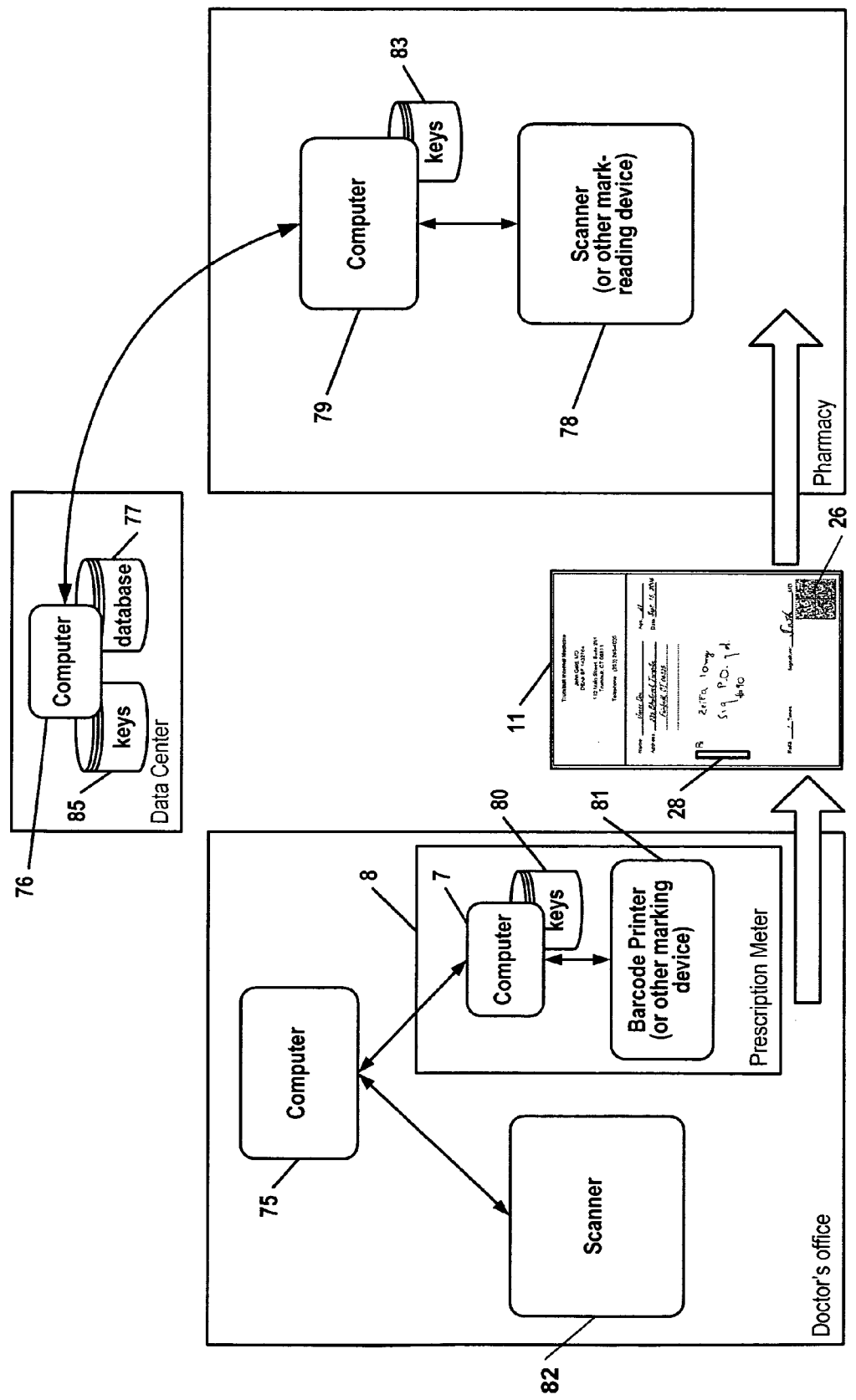
FIG. 4 is a block diagram of an alternate embodiment of this invention.

FIGS. 4, 5A and 5B illustrate an alternate embodiment of this invention which uses an algorithm based on the perceptual hash of portions of a document. This embodiment provides for the verification of the authenticity, integrity and non-repudiation of the document. The perceptual hash of an image is a string of binary data which changes significantly when the image from which it was calculated changes in a way that would be noticeable for a human observer, but it changes very little due to variations of the image typically associated with scanning noise, variation due to skew, scale, luminosity, etc. An example of perceptual hash algorithm is contained in a communication from M. Kivanc Mihcak and Ramarathnam Venkatesan titled "New Iterative Geometric Methods for Robust Perceptual Image Hashing," herein incorporated by reference.

FIG. 4 is a block diagram of an alternate embodiment of this invention. Secure device 8 contains prescription computer 7, bar code printer 81 and secure storage for cryptographic keys 80. Device 8 insures that printer 81 is used only under the control of computer 7 and each instance of printing code 26 contains a unique identifier (for example, the value of an imprint counter) and a digital signature. Computer 7 may be used to generate code 26 using keys 80 and to print code 26 on prescription 11 utilizing printer 81 or any other marking device for example a RFID programming device. In this embodiment, the prescription 11 is scanned by scanner 82. The resulting image file is sent to computer 75. Computer 75 identifies the areas of interest on the prescription image, for example area of interest 640 in FIG. 6A, which contains the handwritten text of the prescribed medication (It is understood that the same method is applicable to printed prescriptions). Computer 75 applies a perceptual hashing algorithm to the image of the area of interest identified previously, resulting in a perceptual image hash. Alternatively, computer 75 may calculate the Gray Scale Profile (GSP) using the algorithm described in FIG. 7. The perceptual image hash (alternatively GSP) is then sent to the computer 7 which is part of the secure device 8. Computer 7 concatenates several pieces of information (for example: the perceptual image hash (alternatively GSP), secure device ID, value of print counter, etc.) resulting in the information payload to be attached to the prescription 11. Additionally, computer 7 calculates a digital signature of the information payload using the encryption keys stored in the secure storage 80. Then, computer 7 generates the information to be attached to the prescription, for example by printing a barcode 26, or by programming a RFID device. This information contains the payload and the digital signature 27 (FIG. 1).

In this embodiment, the prescription 11 is taken to the pharmacy to be filled. The pharmacy wants to verify that the prescription comes from a known prescriber, also the pharmacy wants to know that the content of the prescription 11 was not altered, in particular the area of interest 640 which contains the prescribed items, and lastly, the pharmacy wants to know that the prescription was not used more than the permitted number of times in the same or other pharmacies. At the pharmacy, the prescription 11 is scanned by the scanner 78. The resulting image is sent from the scanner 78 to the computer 79. The computer 79 uses the process described in FIG. 5B to verify the digital signature on computer 79 using keys 83, thus identifying the secure device 8 used by the prescriber to secure the prescription 11.

The computer 79 extracts from code 26 information which uniquely identifies the prescription 11, for example the ID of secure device 8 and the print counter in computer 7. Additional information may be sent from the pharmacy to the datacenter, for example the number of refills allowed. This information may be sent from computer 79 to data center computer 76 and compared with information stored in data center data base 77. The result of this comparison is sent back to the computer 79 to inform the pharmacy if the prescription may be filled or not. Also, this information may be stored in the database 77 for further use. The manner in which code 26 and the digital signature is created and used are described in FIG. 5A and FIG. 5B.

Alternatively, the verification of the digital signature can be performed in a datacenter. In this case, the patient for whom prescription 11 was written or their designee will take prescription 11 to pharmacy scanner 78, where the contents of prescription 11 will be scanned and transmitted to pharmacy computer 79. Computer 79 sends code 26, either as an image or as alphanumeric information to datacenter's computer 76. Computer 76 may use keys 85 to verify the digital signature of code 26 by applying the appropriate cryptographic algorithm. As a result the pharmacy will be assured that the serial number of computer 7 that printed code 26, and the value of a counter which computer 7 increments after each code 26 impression came from a trusted source. This approach eliminates the need to maintain secure cryptographic key storage 83 in each pharmacy, and instead uses the datacenter computer 76 and secure cryptographic key storage 85 to ensure the authenticity of the code 26.

Computer 79 will transmit the record that indicates the prescription identified by code 26 has been used at a given pharmacy to data center computer 76. The foregoing prevents reuse of prescription 11, at a later time in the same or different pharmacy.

FIG. 5A is a flow chart that describes the process which takes place in the prescriber's office to secure the handwritten prescription 11 integrity and authentication. The process begins at step 101, where the physician writes prescription 11 by hand on an ordinary prescription pad. Now the process goes to step 102, where scanner 82 scans prescription 11. Then, in step 102, the image file is transferred to computer 75.

At this point, the process goes to step 104 where areas of interest on prescription 11 are located, i.e., patient information, the medication prescribed, signature, etc. Then, in step 105, an image file is created for the areas of interest.

Next, in step 106, a perceptual hashing algorithm is used to obtain an image hash. Perceptual hashing of an area of interest may be used to ensure the integrity of the area of interest (for example prescription content 640). Ensuring the integrity of an area of interest means verifying that the area of interest was not altered between the time code 26 was attached to the prescription and the time code 26 was processed by the pharmacy's computer 79. Integrity of a document (for example a prescription) is always an important issue as long as the document may be in the possession of parties that cannot be trusted (in this case a patient cannot be trusted by the doctor or pharmacy not to modify the prescription). In the context of cryptography, the integrity of the data is provided by cryptographic hash functions (MD5, SHA-1) in which the data is mapped to short bit strings that make up the hash value, which is then attached to the data. Whenever one would like to test the integrity of the data, one recalculates the hash value from the data itself and compares it to the attached hash value.

Step 107 concatenates the image hash with unique identifiers (identification of computer 7, time/date, the count in the imprint counter in computer 7, prescription 11 identifications, etc.) to create an information payload. Then, step 108 digitally signs the information payload using the assigned cryptographic key from keys 80. Now, in step 109, the information payload is attached to the prescription 11 by printing a barcode 26 on prescription 11. The barcode may be one- or two-dimensional. The information payload may also be programmed into a radio frequency identification device (RFID) attached to prescription 11.

FIG. 5B is a flowchart that describes the process which takes place at the pharmacy to verify the integrity and authenticity of handwritten prescription 11. The process begins in step 150, where scanner 78 scans prescription 11. Next, in step 151, the image file is transferred to computer 79. Then, in step 152, areas of interest on prescription 11, i.e. area of interest 640 which contains the medication prescribed, other areas of interest containing patient information, signature, etc., are located. Then, in step 153, an image file for the areas of interest is created. Then in step 154, a perceptual hashing algorithm is applied (for example to area of interest 640) to obtain an image hash ($H_L$).

In step 156, the areas of interest which contains barcode 26 is located. Then, in step 157, the process reads and decodes the barcode 26, applying any redundancy if needed. Next, in step 159, the digital signature of the information payload is verified.

Step 160 determines whether or not the digital signature is valid. If step 160 determines that the digital signature is not valid, the process goes to step 161, which indicates that verification has failed and there is something wrong with prescription 11. If step 160 determines that the digital signature is correct, the next step in the process will be step 162, where the image hash is extracted from the information payload ($H_p$).

After steps 154 and 162 are completed, step 155 will calculate the distance D between in the perceptual hash of the image calculated locally ($H_L$) and the perceptual hash of the image calculated in the prescriber's office and found in the information payload ($H_p$). The distance D between ($H_L$) and ($H_p$) is obtained by utilizing the method described in the Arun Qamra, et. al article entitled "Enhanced Perceptual Distance Functions And Indexing For Image Replica Recognition", published in the March 2005, issue of IEEE Transactions On Pattern Analysis And Machine Intelligence, Vol. 27, No. 3, herein incorporated by reference.

Then in step 165, the process will compare the distance D with the acceptable threshold T. An acceptable threshold is empirically determined by the application in which it is used. Then, in step 166, the process will determine whether or not the distance D is less than or equal to the acceptable threshold T. If step 166 determines that the distance D is not less than or equal to the acceptable threshold T, step 167 indicates that the verification has failed and there is something wrong with prescription 11, most likely the prescription was altered.

If step 166 determines that the distance D is less than or equal or equal to the acceptable threshold T, the next step is step 168, where prescription identifiers ($P_{ID}$) from the information payload (device identification, the time/date, imprint counter, physician's identification, etc.) are extracted.

At this point in process, step 169 requests from data center computer 76 confirmation that this ($P_{ID}$) can be accepted. Then, step 170 determines whether or not $P_{ID}$ may or may not be accepted. If step 170 determines that $P_{ID}$ cannot be accepted, step 171 will indicate that the verification has failed and there is something wrong with prescription 11. If step 170 indicates that ($P_{ID}$) is accepted, then step 172 will indicate that the verification is successful and prescription 11 is a valid prescription.

FIGS. 4, 6A, 6B, 6C, 6D, 6E, 6F, 6G, 6H, 7, 8A and 8B illustrate another embodiment of this invention which uses an algorithm based on the gray scale profile of portions of a document instead of the perceptual hash of an image which was described previously. This embodiment provides for the verification of the authenticity, integrity and non-repudiation of the document.

Figures 6A, 6B:
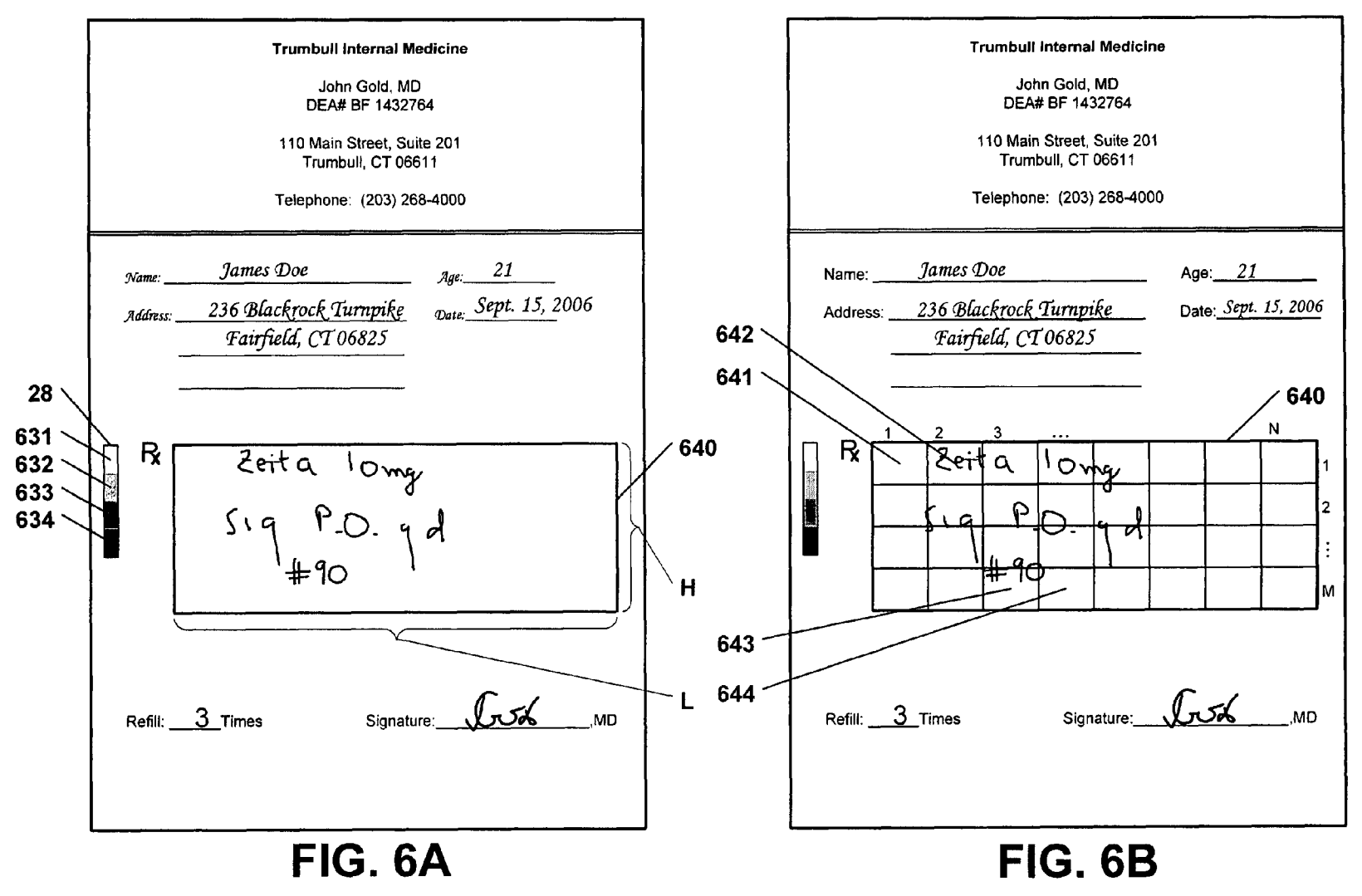

FIG. 6A is a drawing of prescription 11 of FIG. 1 containing reference gradient strip 28 and an area of interest 640. Gradient strip 28 contains four tone levels 631, 632, 633 and 634. Levels 631, 632, 633 and 634 have varying proportions of white and black, to give a full range of grays between white and black. Gradient strip 28 may be divided into additional levels to represent different levels of gray. Area of interest 640 has a length equal to L and a height equal to H. Area 640 contains information regarding the medication prescribed by Physician Gold, namely the medication Zeita its dosage instructions regarding the use of the Zeita and 90 tablets should be supplied each time the prescription is filled. It would be obvious to one skilled in the art that additional areas of interest may be used, i.e., areas representing information regarding the patient, areas representing the physician's signature, areas representing the number of refills, etc.

FIG. 6B is a drawing of prescription 11 illustrating the segmentation of area of interest 640 into elements. Area of interest 640 is divided into N×M sub-sections or elements. N and M are the number of columns and rows, respectively. In FIG. 6B, N=8 and M=4. No material appears in element 641 and the letters "Z, e, i" and a portion of the letter "t" appears in element 642. Portions of the "#" sign and portions of the numerals "9 and 0" appear in element 643. Portions of the numeral "0" appear in element 644.

Figures 6C, 6D:
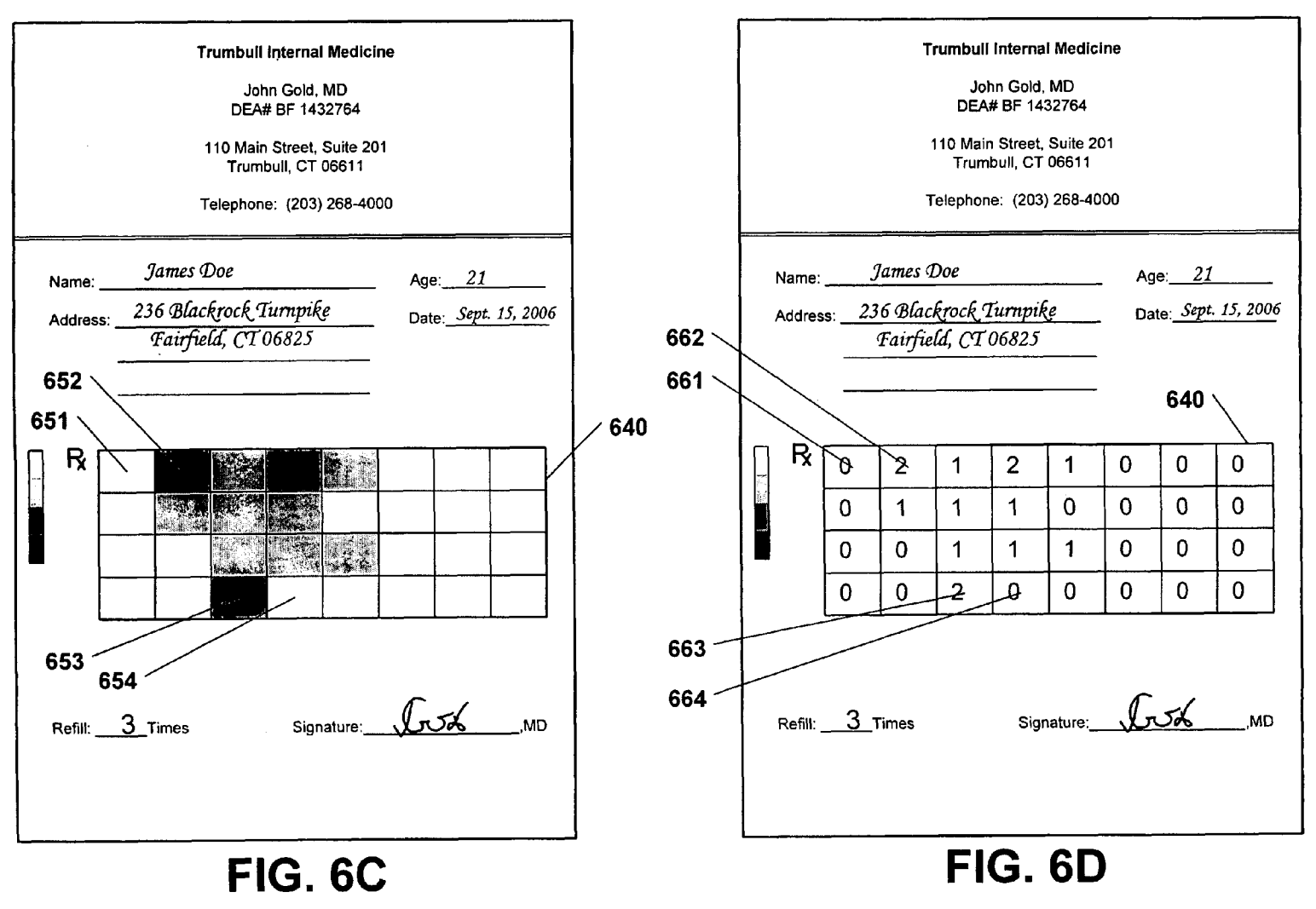

FIG. 6C is a drawing of prescription 11 illustrating the assignment of gray levels for each element to the closest reference gray level found on the gradient strip 28. Element 651 appears to have the tone shown in level 631 and element 652 appears to have the tone shown in level 633. Element 653 appears to have the tone shown in level 633 and element 654 appears to have the tone shown in level 631.

FIG. 6D is a drawing of prescription 11 illustrating the assignment of index numbers corresponding to the closest reference gray levels appearing in gradient strip 28. Level 631 is assigned index number "0' and level 632 is assigned index number "1". Level 633 is assigned index number "2' and level 634 is assigned index number "3"; It would be obvious to one skilled in the art that additional index numbers may be used when there are additional gray scale levels appearing in strip 28. Element 661 has the index number indicated by level 631 and element 662 has the index number indicated by level 633. Element 663 has the index number indicated by level 633 and element 664 has the index number indicated by level 631

FIG. 6E is a drawing of an altered version of prescription 11. Note in area of interest 640, the number of tablets prescribed has been increased from '90" to "900".

FIG. 6F is a drawing of an altered version of prescription 11 illustrating the segmentation of area of interest 640 into elements 671, 672, 673 and 674. No material appears in element 671 and the letters "Z, e, i" and a portion of the letter "t" appears in element 672. Portions of the "#" sign and portions of the numerals "9 and 0" appear in element 673. Portions of the added numeral "0" and almost the complete numeral "0" appear in element 674.

Figures 6G, 6H:
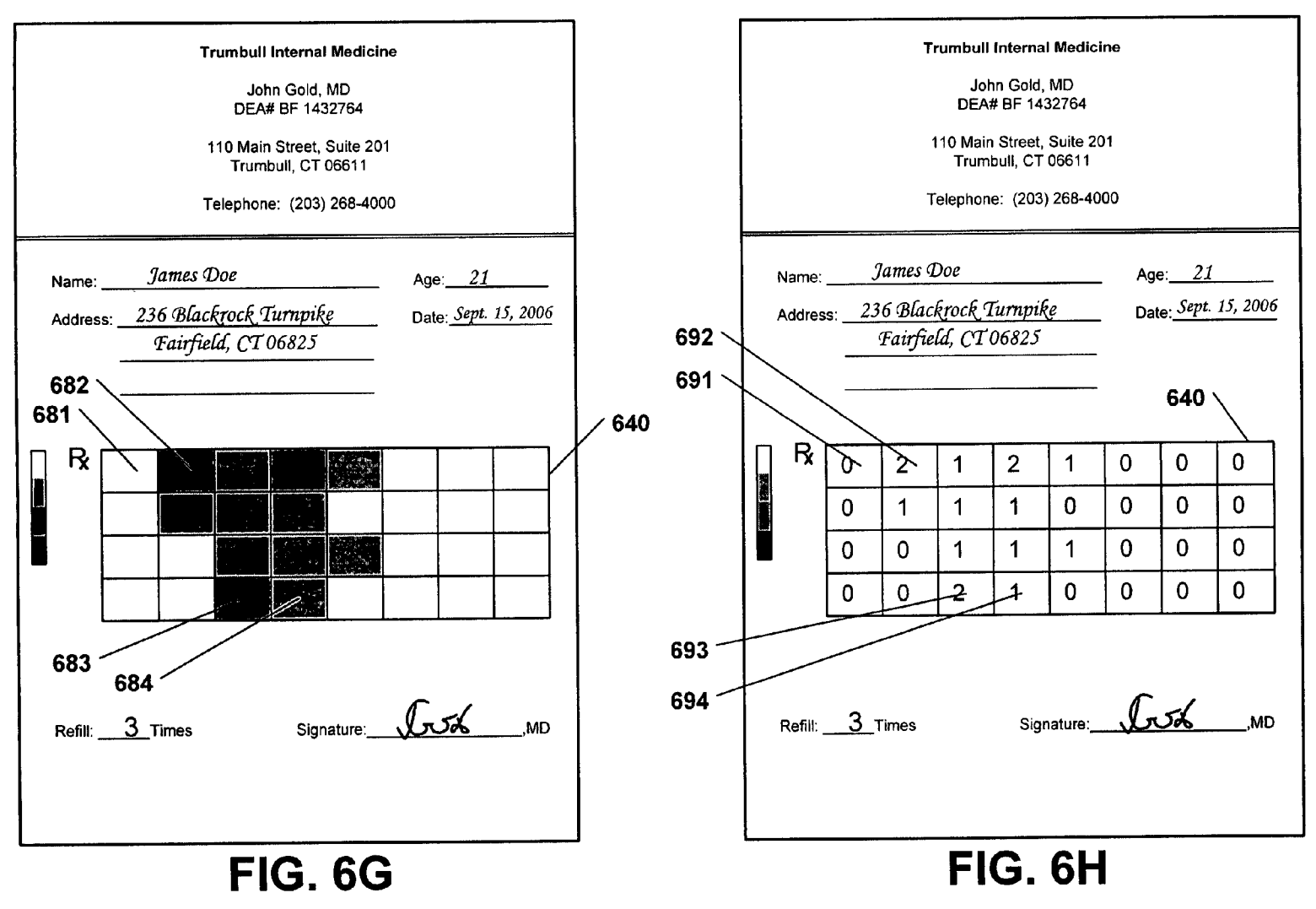

FIG. 6G is a drawing of an altered prescription 11 illustrating the assignment of gray levels for each element to the closest reference gray level found on the reference gradient strip 28. Element 681 appears to have the tone shown in level 631 and element 682 appears to have the tone shown in level 633. Element 683 appears to have the tone shown in level 633 and element 684 appears to have the tone shown in level 632. Note in FIG. 6C element 654 had the tone shown in level 631.

FIG. 6H is a drawing of an altered prescription 11 illustrating the assignment of index numbers corresponding to the closest reference gray level appearing in gradient strip 28. Element 691 has the index number indicated by level 631 and element 692 has the index number indicated by level 633. Element 693 has the index number indicated by level 633 and element 694 has the index number indicated by level 633. Note in FIG. 6D element 664 had a "0" which indicates the index number of level 631 and now element 694 has a "1" which indicates the index number of level 632. Thus, this is an indication that the prescription 11 has been altered.

Figure 7:
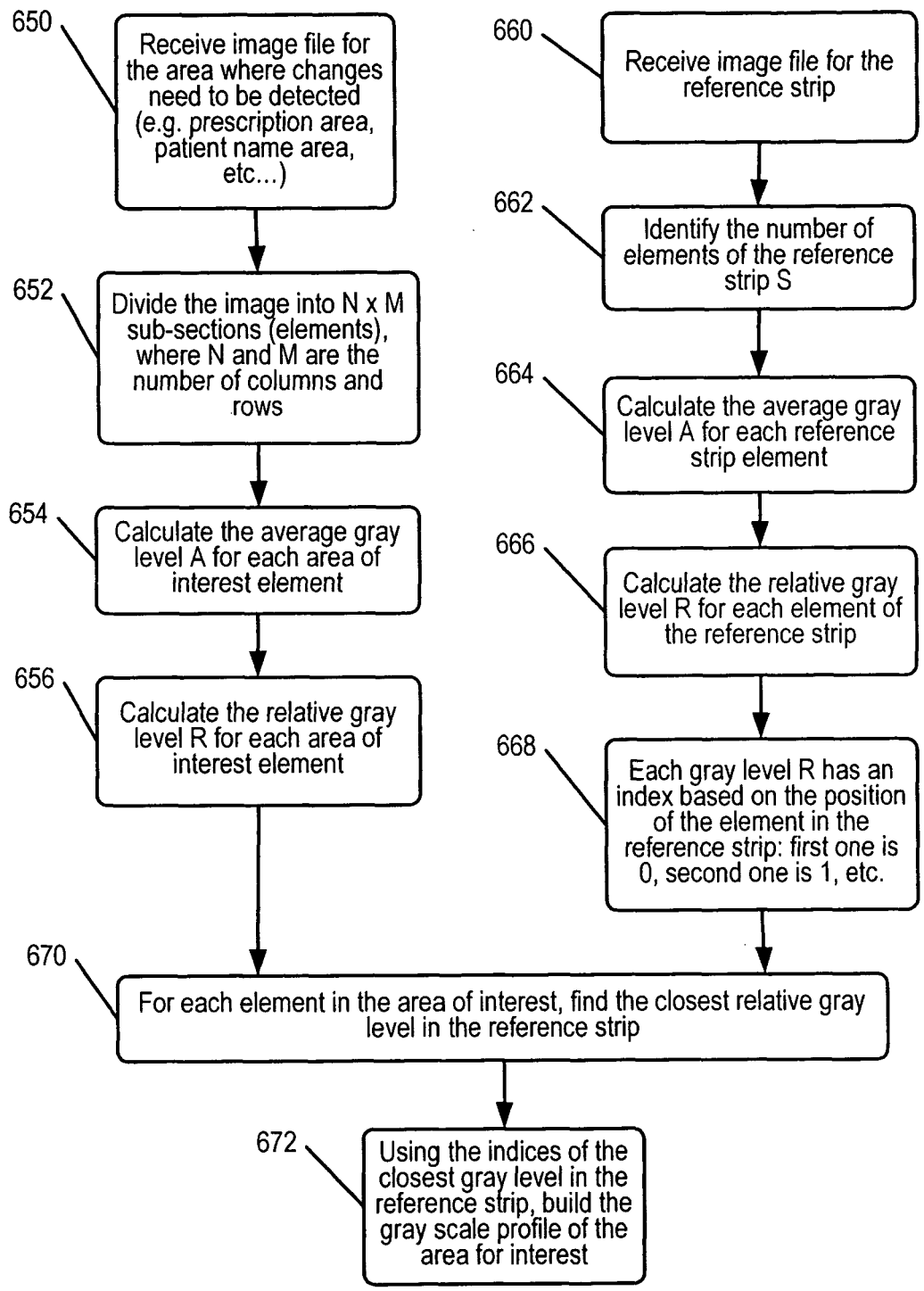
FIG. 7 is a flowchart describing the gray scale profile (GSP) algorithm.

FIG. 7 is a flowchart that describes the grey scale profile (GSP) algorithm. The GSP algorithm receives as input an image (of the area of interest), the number of rows and the number of columns. The algorithm divides the image into N×M elements and produces as output a set of numbers that are indexes into an array of gray levels, one number for each element of the area of interest.

The process begins in step 650 where the image file for the areas where changes need to be detected on prescription 11 i.e., the prescription area 29, the patient's name, area, etc. Then in step 652 the image from area 29 is divided into N×M subsections "elements", where N and M are the number of columns and rows. Next in step 654 the average grey level for each area of interest for each element is calculated. Then in step 656 the relative grey level R for each element in the area of interest is calculated.

In step 660 an image file of the reference grey scale strip is received. In step 662 the number of elements of the reference strip is obtained. In FIG. 6A the number of elements is four. S is the number of elements in the reference strip (S=4 in FIG. 6A). Then in step 664 the average grey level for each reference strip element is calculated. Next in step 666 the relative grey level R for each element of the reference strip is calculated. In step 668 each grey level R has an index based on the position of the element in the referenced strip: first one is a zero, the second one is a one, etc. In FIG. 6A, the index of element 631 is 0, the index of element 632 is 1, the index of element 633 is 2 and the index of element 634 is 03.

After steps 656 and 668 are completed, step 670 will for each element in the area of interest, find the closest relative grey level in the reference strip. Next step 672 will use the indices of the closest grey level in the reference strip, to build the grey scale profile of the area of interest.

The aforementioned flowchart may be expressed mathematically by the following Gray Scale Profile algorithm.

The Gray Scale Profile (GSP) algorithm receives as input an image (of the area of interest 640), the number of rows "N" and the number of columns "M" and produces as output a set of numbers that are indexes into an array of gray levels, one number for each element of the area of interest.

The algorithm receives an image file for the area where changes need to be detected (e.g. prescription area, patient name area, number of refills, etc. . . . ). Assume that the area of interest is rectangular. If it is not rectangular, the algorithm can be modified to create sub-sections of other shapes, but the general idea can be maintained.

The dimensions of the area of interest are L and H, length and height, respectively.

The next step is to divide the image into N×M sub-sections (elements). N and M are the number of columns and rows, respectively. In FIG. 6B, N=8 and M=4.

The scanning resolution is R, measured in dots per inch. For simplicity, we can assume that the horizontal resolution is the same with the vertical resolution. The scanner and scanning software subsystem creates an image with $2^B$ gray levels. Thus, each pixel is represented by a number P using B bits. P takes values between 0 and $(2^B-1)$. For example, in an image using 2 bits per pixel, the darkest pixel (black) will be (0, 0) and the lightest pixel (white) will be (1, 1). For black, P=0 and for white P=3.

Each scanned pixel has a P value as described above. Within a given element, we use the notation Pij for the value corresponding to the pixel on row i and column j.

The number of pixels in each element is ((L/N)*R)×((H/M)*R). For example, if R=100 dpi, L=4 inches, H=2 inches and we chose to have 8 columns (N=8) and 4 rows (M=4), then each elements' dimensions in pixels are (L/N)*R=4/8*100=50 pixels horizontally, and (H/M)*R=2/4*100=50 pixels vertically. In this example, each element is a square 50 by 50 pixels.

We define the average gray level (A) for an element to be the number obtained by calculating the sum of the P numbers for all pixels in the given element and dividing by the number of pixels.

$$A_{element} = \frac{\sum_{i=1}^{\frac{L}{N}*R} \sum_{j=1}^{\frac{H}{M}*R} Pij}{\left(\frac{L}{N}*R\right)*\left(\frac{H}{M}*R\right)}$$

Hence, the $A_{element}$ is a number between 0 and $2^B-1$.

The relative gray level R (expressed in percentages) is:

$$R_{element} = \frac{A}{2^B} * 100$$

The algorithms uses a strip containing reference gray levels (28 in FIG. 6A), which was previously applied/printed on the document. This strip is a set of rectangular elements printed such that they have their R numbers spaced equally between 0 and 100%. Each element of the strip is assigned a sequence number from 0 to $2^B-1$. In FIG. 1, B=2, resulting in four elements numbered 0, 1, 2, and 3. The values of R for each of these elements is in the middle of each interval. For example, in FIG. 1, the strip 28 has four elements that are intended to generate the following R numbers: $R_0$=12.5%, $R_1$=37.5%, $R_2$=62.5% and $R_3$=87.5%. These values are selected in the middle of the four intervals corresponding to 0-25%, 25%-50%, 50%-75% and 75%-100%. We will refer to these number as 'theoretical' values of R.

The reference gray levels are used to limit the variability introduced by printing and scanning devices and to ensure a consistent measurement of relative intensity of each element in the area of interest, for example where the prescription is written.

Next step is to scan the reference strip under the same conditions used to scan the area of interest. This is best achieved by scanning the entire document and isolating the areas or interest as portions of the scanned image. Identify the number of elements S of the reference strip. In the above example S=4.

For each image of an element in the reference strip (28) we calculate $R_{element}$. Due to the variability of printing and scanning devices, the actual R numbers obtained may be different from the theoretical values. We will refer to these values as reference R numbers $R_{element}^{reference}$. In the above example illustrated in FIG. 6A, there are four elements or levels in the reference strip (631, 632, 633, 634) and their R values are:

$R_0^{reference}$, $R_1^{reference}$, $R_2^{reference}$, and $R_3^{reference}$ for each element in the area of interest 640 we calculate $R_{element}$ and find the closest $R^{reference}$ number. We then assign to the given element the index of the closest $R^{reference}$ number. FIG. 6D illustrates the result of assigning the index number of the closest reference gray level. For example the element 661 in the upper left corner of the area of interest 640 is assigned gray level 0, while the element 662 immediately to its right is assigned gray level 2, as shown in FIG. 6D By simply looking at the amount of text which is covered by each of these two elements, one can notice that the first element has no writing in it (hence its gray level 0) and the second element contains the first four letters of the drug being prescribed ("Zeit"), hence the level is 2.

As a result of the assignment in previous step, a N×M array of numbers is generated, as shown in FIG. 6D. This array is the Gray Scale Profile for the given area of interest and it is the output of the algorithm.

The distance between two gray scale profiles, for example, the first GSP being obtained by processing the image scanned in the prescriber's office and the second GSP being obtained by processing the image scanned at the pharmacy can be computed as follows.

The gray scale profile can be expressed as an array of numbers. For a two-dimensional array, the elements of a first array are expressed as:

$$Uij$$

Two GSP can be compared if they generate profiles of the same dimensions. If the elements of a second array are $$Vij$$

than, the distance between the first array and the second array can be expressed by:

$$D = \sum_{i,j} |Uij - Vij|$$

Many other measures of this distance are available and practical considerations may dictate which is most appropriate.

Figure 8A:
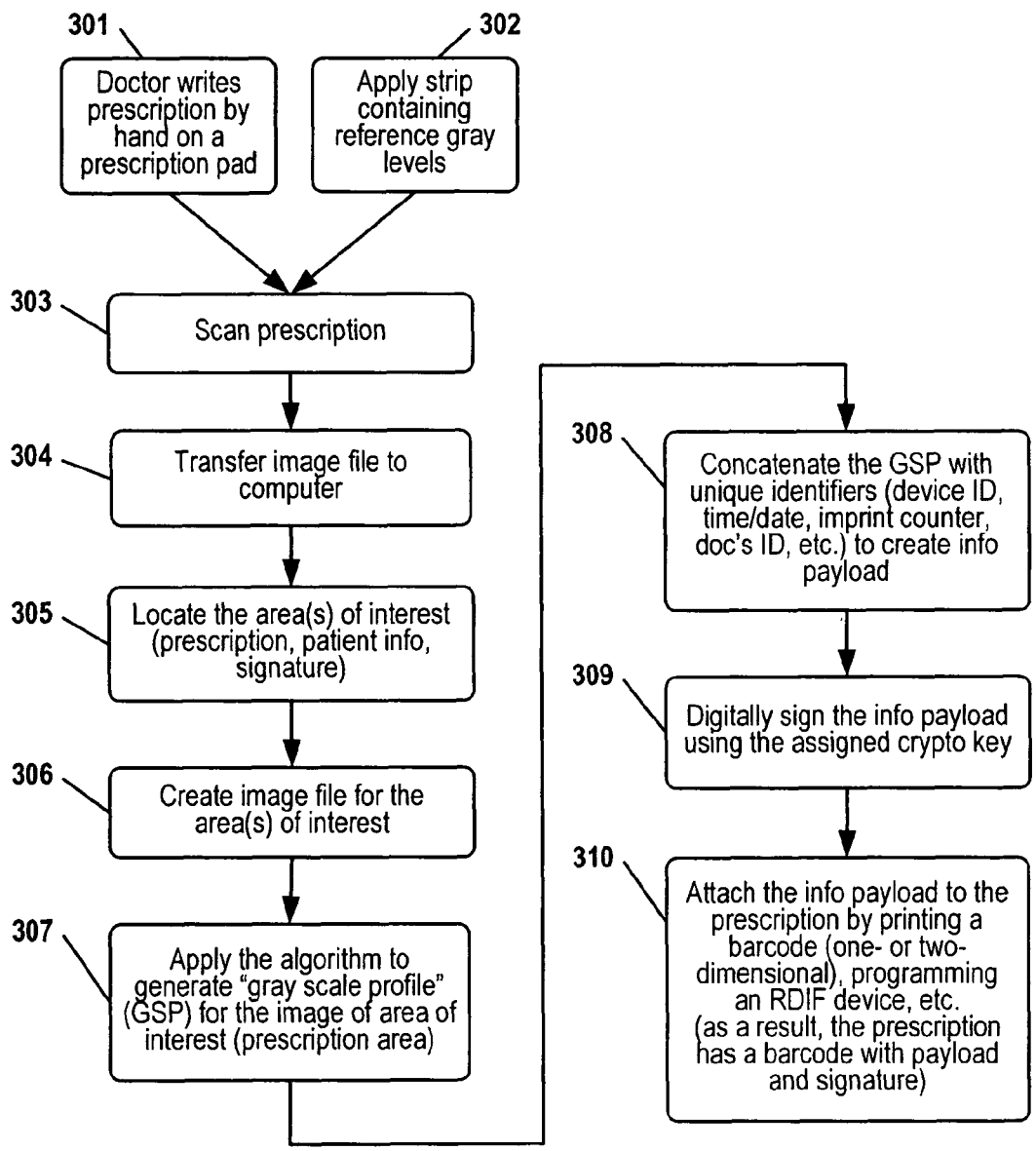
FIG. 8A is a flowchart that describes the process to secure the handwritten prescription 11 for the purpose of authentication, integrity and to prevent replay, used in an embodiment of this invention using gray scale profile (GSP) algorithm.

FIG. 8A is a flow chart that describes the process to secure the hand written prescription 11 to the purpose of authentication, integrity and to prevent unauthorized use, including the grey scale profile algorithm. The process begins at step 301 where the physician writes prescription 11 by hand on a prescription pad. In step 302 a gradient strip 28 containing reference gray levels is applied to prescription 11. Then in step 303 scanner 82 scans prescription 11. Then in step 304 scanner 82 transfers the image file to computer 75. At this point in step 305 areas of interest on prescription 11 are located, i.e., the specifics of the prescription, patient information, the physician's signature, etc. Next in step 306 an image file is created for the areas of interest. Step 307 applies the grey scale profile algorithm to generate a grey scale profile for the image of the areas of interest, i.e., the area that describes the prescribed medication.

Step 308 concatenates the grey scale profile 28 with unique identifiers, i.e., the identification of the computer, the time/date, the value of a counter which computer 7 increments after each code 26 impression came from a trusted source, the identification of the physician who wrote prescription 11, etc. to create an information payload. Step 309 then digitally signs the information payload using the assigned cryptographic keys 80. Now, in step 310, the information payload is attached to the prescription 11 by printing barcode 26, which may be one or two dimensional on prescription 11. The information payload may also be programmed into a Radio Frequency Identification Device "RFID" attached to prescription 11.

Figure 8B:
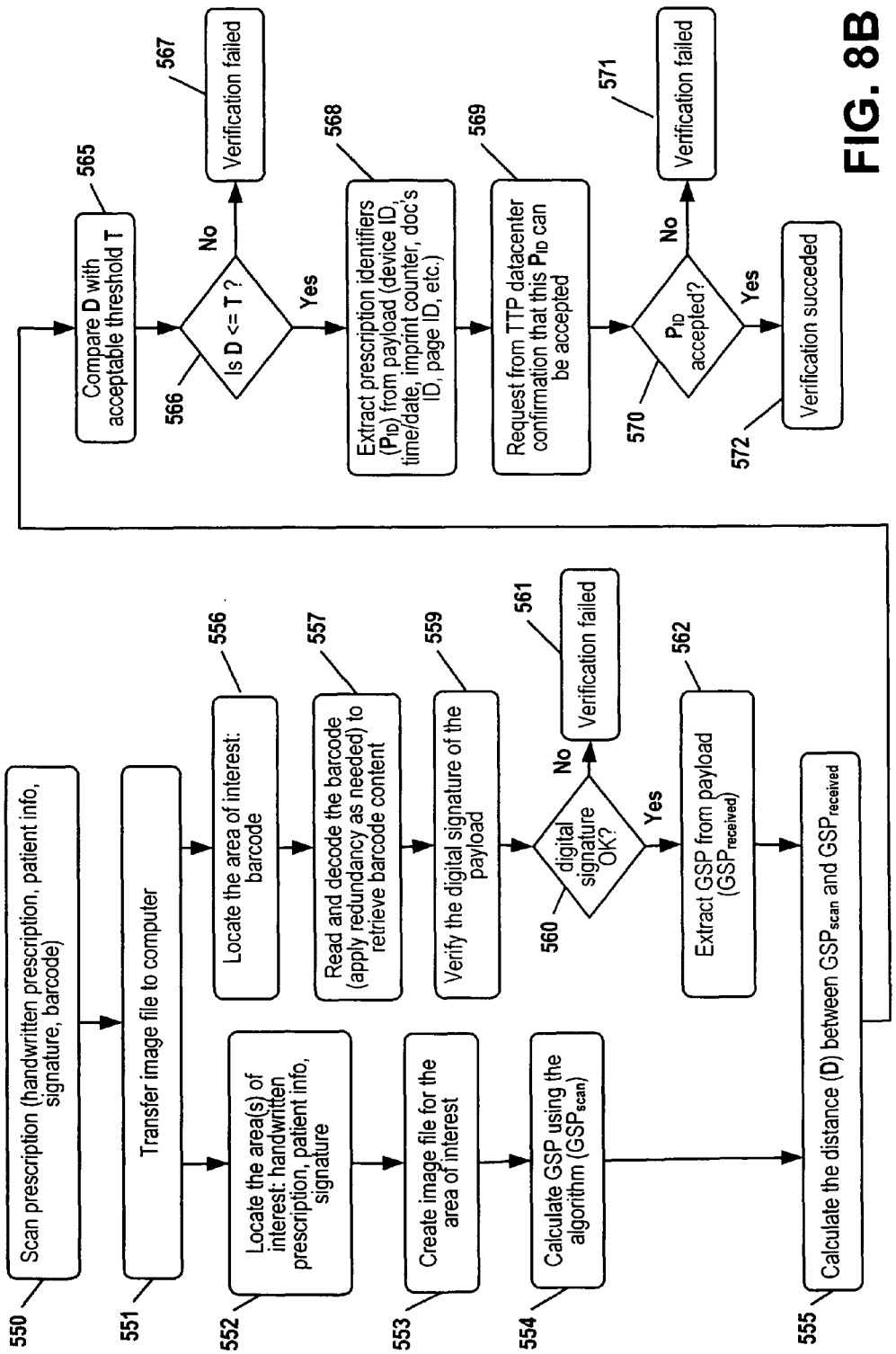
FIG. 8B is a flowchart that describes the pharmacy's process to verify the handwritten prescription 11 authentication, integrity and to prevent replay, used in an embodiment of this invention using gray scale profile (GSP) algorithm.

FIG. 8B is a flow chart that describes the pharmacy's process to verify the handwritten prescription 11 authentication, integrity and to unauthorized use, including the GSP algorithm. The process begins in step 550 where scanner 78 scans prescription 11 to obtain relevant information from prescription 11, i.e., patient information, the physician's signature, barcode 26. Then in step 551 scanner 78 transfers the image file to computer 79. Next in step 552 the areas of interest on prescription 11 are located i.e., patient information, the physician's signature. Next in step 553 an image file is created for the areas of interest. Then step 554 uses the grey scale profile algorithm to calculate the scanned grey scale profile.

After steps 554 and 562 are completed, step 555 will calculate the distance D between the gray scale profile of the image scanned in the pharmacy ($GSP_{scan}$) and gray scale profile of the image scanned in the prescriber's office and received in the code 26 ($GSP_{received}$).

The distance D may be calculated by Comparing corresponding points of the two profiles, as described in a subsequent paragraph. In step 565, the process will compare the distance D with the acceptable threshold T. An acceptable threshold is empirically determined by the application in which it is used. Then, in step 566, the process will determine whether or not the distance D is less than or equal to the acceptable threshold T. If step 666 determines that the distance D is not less than or equal to the acceptable threshold T, step 567 indicates that the verification has failed and there is something wrong with area of interest 640.

If step 566 determines that the distance D is less than or equal or equal to the acceptable threshold T, the next step is step 568, where prescription identifiers ($P_{ID}$) from the information payload (device identification, the time/date, imprint counter, physician's identification, etc.) are extracted.

At this point in the process, step 569 requests from data center computer 76 confirmation that this ($P_{ID}$) can be accepted. Then, step 570 determines whether or not $P_{ID}$ may or may not be accepted. If step 670 determines that $P_{ID}$ cannot be accepted, step 571 will indicate that the verification has failed and there is something wrong with area of interest 640. If step 670 indicates that ($P_{ID}$) is accepted, then step 672 will indicate that the verification is successful and area 640 is genuine.

The above specification describes a new and improved method for the preparation and securing of prescriptions. It is realized that the above description may indicate to those skilled in the art additional ways in which the principles of this invention may be used without departing from the spirit. Therefore, it is intended that this invention be limited only by the scope of the appended claims.

What is claimed is:

1. A method for creating a document that allows for authenticating and verifying integrity of the document, the method comprising:
    receiving, by a processing device, an image of the document having an area of interest containing information that varies from other documents of a same type;
    segmenting, by the processing device, the area of interest on the document into a plurality of elements;
    obtaining, by the processing device, an average gray scale of each element;
    determining, by the processing device, a relative gray scale for each element by matching the average gray scale of each element of the area of interest to as closest element of a reference gradient strip having a plurality of gray scales;

generating, by the processing device, a gray scale profile of the area of interest based on the relative gray scale for each element;

inserting, by the processing device, the gray scale profile into an identifier; and printing, by a printing device, the identifier and the gradient strip on the document.

2. The method claimed in claim 1, further comprising:

generating, by the processing device, a digital signature; and inserting the digital signature into the identifier.

3. The method claimed in claim 2, further comprising verifying the document, wherein verifying the document comprises:

scanning, by a scanning device of a verification system, the document having the printed identifier and gradient strip thereon to obtain an image of the document;

obtaining, by a processing device of the verification system, contents of the identifier from the image including the gray scale profile;

obtaining, by the processing device of the verification system, the area of interest of the document from the image;

segmenting, by the processing device of the verification system, the area of interest obtained from the image into a plurality of elements;

obtaining, by the processing device of the verification system, an average gray scale of each element in the area of interest obtained from the image;

determining, by the processing device, a relative gray scale of each element in the area of interest obtained from the image by matching the average gray scale of each element of the area of interest to the closest element of the gradient strip;

generating, by the processing device, a gray scale profile of the area of interest obtained from the image;

comparing, by the processing device of the verification system, the gray scale profile of the area of interest obtained from the image with the corresponding gray scale profile that was inserted in the identifier; and determining, by the processing device of the verification system, if the gray scale profile of the area of interest obtained from the image deviates from the gray scale profile that was inserted into the identifier.

4. The method claimed in claim 3, further comprising:
verifying the digital signature contained in the identifier.

5. The method claimed in claim 3, further comprising:
sending the identifier to a datacenter; and
verifying the digital signature contained in the identifier.

6. The method claimed in claim 3, further comprising:
sending at least a portion of the identifier to a datacenter; and
comparing the at least a portion of the identifier to previously used identifiers stored at the database to determine if the document has already been verified.

7. The method claimed in claim 3, wherein determining if the gray scale profile of the area of interest obtained from the image deviates from the gray scale profile that was inserted into the identifier further comprises:
calculating a distance between the gray scale profile of the area of interest obtained from the image and the gray scale profile inserted in the identifier; and
comparing the distance with a threshold.

8. The method claimed in claim 1, further comprising:
assigning a value to each gray scale on the gradient strip.

9. The method claimed in claim 1, wherein the document is a prescription for an item.

10. The method claimed in claim 9, wherein the area of interest contains information about the item prescribed.

11. The method claimed in claim 9, wherein the prescription is associated with a patient, and the area of interest contains information about the patient.

12. The method claimed in claim 9, wherein the area of interest contains a prescriber's signature.

13. The method claimed in claim 1, wherein the plurality of elements are rectangles.

14. The method claimed in claim 1, wherein at least a portion of the document is handwritten.

15. The method claimed in claim 1, wherein at least a portion of the document is generated by a computer.

\* \* \* \* \*